(12) United States Patent
Rigaut et al.

(10) Patent No.: US 10,583,154 B2
(45) Date of Patent: Mar. 10, 2020

(54) MULTI-DOSE COMPOSITIONS CONTAINING AN ANTIMICROBIAL POLYAMIDE OR OCTENIDINE PRESERVATIVE

(71) Applicants: BOEHRINGER INGELHEIM ANIMAL HEALTH USA INC., Duluth, GA (US); GENZYME CORPORATION, Cambridge, MA (US)

(72) Inventors: Guillaume Rigaut, Lyons (FR); Celine Loss-Dunod, Charly (FR); Alexis Guy Andre Lucien Parisot, Lyons (FR); Pradeep K. Dhal, Bridgewater, NJ (US)

(73) Assignees: Boehringer Ingelheim Animal Health USA Inc., Duluth, GA (US); GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/487,323

(22) Filed: Apr. 13, 2017

(65) Prior Publication Data
US 2017/0296577 A1 Oct. 19, 2017

Related U.S. Application Data

(60) Provisional application No. 62/322,258, filed on Apr. 14, 2016.

(51) Int. Cl.
| | | |
|---|---|---|
| *A61K 31/787* | (2006.01) | |
| *A61K 47/18* | (2017.01) | |
| *A61K 47/34* | (2017.01) | |
| *A61K 31/444* | (2006.01) | |
| *A61K 39/04* | (2006.01) | |
| *A61K 39/12* | (2006.01) | |
| *C12N 7/00* | (2006.01) | |
| *A61K 39/00* | (2006.01) | |
| *A61K 39/02* | (2006.01) | |

(52) U.S. Cl.
CPC .......... *A61K 31/787* (2013.01); *A61K 31/444* (2013.01); *A61K 39/04* (2013.01); *A61K 39/12* (2013.01); *A61K 47/186* (2013.01); *A61K 47/34* (2013.01); *C12N 7/00* (2013.01); *A61K 39/0241* (2013.01); *A61K 2039/54* (2013.01); *A61K 2039/552* (2013.01); *A61K 2039/55566* (2013.01); *C12N 2750/10034* (2013.01)

(58) Field of Classification Search
CPC .... A61K 31/787; A61K 31/444; A61K 39/04; A61K 39/12; A61K 39/0241; A61K 47/186; A61K 47/34; A61K 2039/54; A61K 2039/552; A61K 2039/55566; C12N 7/00; C12N 2750/10034
See application file for complete search history.

(56) References Cited

U.S. PATENT DOCUMENTS

| | | | |
|---|---|---|---|
| 9,095,567 B2 | 8/2015 | Khandke et al. | |
| 2006/0127499 A1* | 6/2006 | Lazarev | A61K 45/06 424/638 |
| 2014/0271526 A1* | 9/2014 | Cady | A61K 31/787 424/78.3 |
| 2016/0208046 A1 | 7/2016 | Dhal et al. | |

OTHER PUBLICATIONS

Archana, editor. Vaccinophobia and Vaccine Controversies of the 21$^{st}$ Century. ISBN 978-1-4614-7437-1—Springer New York Heidelberg Dordrecht London.
Bis et al. Antimicrobial preservatives induce aggregation of interferon alpha-2a: The order in which preservatives induce protein aggregation is independent of the protein. International Journal of Pharmaceutics 472 (2014) 356-361.
Guo et al. Preservative Formulation and Effectiveness in Oral Solutions and Suspensions. PDA Metro Meeting, Feb. 15, 2011.
Meyer et al. Antimicrobial Preservative Use in Parenteral Products: Past and Present. Journal of Pharmaceutical Sciences, vol. 96, No. 12, Dec. 2007.
"7bq5a" Inclusion of Antioxidants and antimicrobial preservatives in medicinal products. pp. 177-182. Directive 81/852/EEC as amended Jul. 1997.

* cited by examiner

*Primary Examiner* — Blessing M Fubara
(74) *Attorney, Agent, or Firm* — Judy Jarecki-Black; John Ezcurra

(57) ABSTRACT

The present invention relates to non-mercurial preservatives, including antimicrobial polyamide polymers and octenidine, and to methods of use thereof to produce preservative-containing multi-dose formulations. The preservative-containing multi-dose formulations exhibit resistance to one or more contaminating microorganisms, and have advantageous properties with respect to long term stability of biological and small molecule active ingredients.

15 Claims, No Drawings

MULTI-DOSE COMPOSITIONS CONTAINING AN ANTIMICROBIAL POLYAMIDE OR OCTENIDINE PRESERVATIVE

CROSS-REFERENCE TO RELATED APPLICATIONS

This application claims priority to U.S. provisional application No. 62/322,258, filed on 14 Apr. 2016, and incorporated herein by reference in its entirety.

INCORPORATION BY REFERENCE

This application makes reference to US 2014/0271526 and US 2014/0275469, the disclosures of which are incorporated by reference herein in their entireties. All documents cited or referenced herein are likewise incorporated herein by reference, and may be employed in the practice of the invention.

Field of the Invention

The disclosure relates to thimerosal-free preservatives for multi-dose formulation. The preservatives include antimicrobial polyamides and octenidine.

Background of the Invention

For multi-dose formulations including vaccines, preservatives are required to minimize contamination of the composition of subsequent doses after the first dose is used. The preservative must enable the vaccine formulation to pass efficacy tests or antimicrobial challenge tests according to the United States Pharmacopeia (USP) in the U.S., British Pharmacopeia (BP), and European Pharmacopeia (EP) in Europe.

Thimerosal is a commonly-used preservative in vaccines. Thimerosal is a mercurial compound that is potentially irritating, and may increase the chance of allergic reactions. Thimerosal is also undesirable for the environment.

Accordingly, it would be advantageous to find new and safer preservatives for vaccines to replace thimerosal. In this application, Applicants disclose inter alia the use of antimicrobial polyamide compounds and octenidine as preservatives for vaccines. The highly effective preservatives are non-irritating and contain no mercurial compounds.

SUMMARY OF THE INVENTION

In one aspect, the invention provides safe and effective thimerosal-free preservative for multi-dose formulations including vaccines. In an embodiment, the preservative may comprise water soluble, antimicrobial, amine functional polyamides, having the general structure as set forth in formulae I-V (below). These polymers may be produced using the methods described in US 2014/0275469 and U.S. Pat. No. 9,326,994 B2 (to Genzyme).

In an embodiment, the polyamide is a compound of Formula (I):

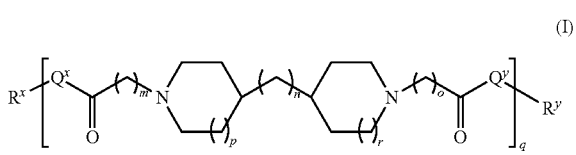

(I)

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
viii) $Q^y$ is NH—$R^w$, NH—$CH_2$—$R_w$, $(C_1-C_{10})$alkyl, or $(C_6-C_{14})$aryl,
wherein $R^w$ is absent or a $(C_1-C_{10})$alkyl, $(C_2-C_9)$heteroalkyl, $(C_6-C_{14})$aryl, or $(C_2-C_9)$heteroaryl;
ix) $R^x$ and $R^y$ are each independently a pharmaceutically acceptable end group.

In another embodiment, the polyamide has the structure of Formula (II):

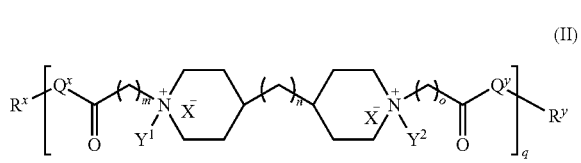

(II)

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
viii) $Q^y$ is NH—$R^w$, NH—$CH_2$—$R_w$, $(C_1-C_{10})$alkyl, or $(C_6-C_{14})$aryl,
wherein $R^w$ is absent or a $(C_1-C_{10})$alkyl, $(C_2-C_9)$heteroalkyl, $(C_6-C_{14})$aryl, or $(C_2-C_9)$heteroaryl;
ix) $R^x$ and $R^y$ are each independently a pharmaceutically acceptable end group;
x) $X^-$ is each independently a halo or any pharmaceutically acceptable anion;
xi) $Y^1$ and $Y^2$ are each independently H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —S—O—$(C_1-C_{10})$alkyl, —O(O)C—$(C_1-C_{10})$alkyl, —$(C_1-C_{10})$alkyl-COOH, $(C_3-C_{10})$cycloalkyl-COOH, —(O)$CH_3$, —OH, amide, a dihydroxy group, represented by Formula (D),

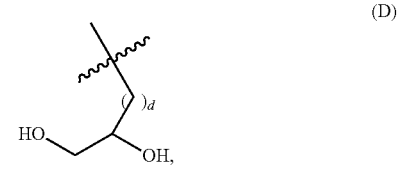

(D)

wherein d is an integer from 0 to 25, or a polyethylene glycol group, represented by Formula (E)

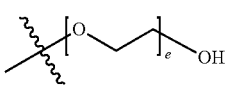

wherein e is an integer from 1 to 25.

In another embodiment, the polyamide has the structure of Formula (III):

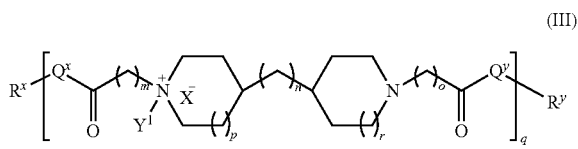

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
viii) $Q^y$ is NH—$R^w$, NH—CH$_2$—$R_w$, $(C_1-C_{10})$alkyl, or $(C_6-C_{14})$aryl,
wherein $R^w$ is absent or a $(C_1-C_{10})$alkyl, $(C_2-C_9)$heteroalkyl, $(C_6-C_{14})$aryl, or $(C_2-C_9)$heteroaryl;
i) $R^x$ and $R^y$ are each independently a pharmaceutically acceptable end group;
ix) $X^-$ is each independently a halo or any pharmaceutically acceptable anion;
x) $Y^1$ is H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —S—O—$(C_1-C_{10})$alkyl, —O(O)C—$(C_1-C_{10})$alkyl, —$(C_1-C_{10})$alkyl-COOH, $(C_3-C_{10})$cycloalkyl-COOH, —(O)CH$_3$, —OH, amide, a dihydroxy group, represented by Formula (D),

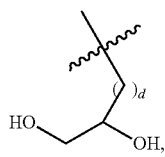

wherein d is an integer from 0 to 25, or
a polyethylene glycol group, represented by Formula (E),

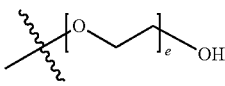

wherein e is an integer from 1 to 400.

In another embodiment, the polyamide has the structure of Formula (IV):

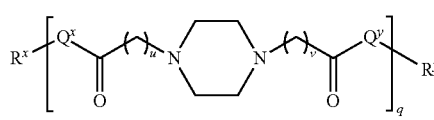

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—CH$_2$—$R_w$, $(C_1-C_{10})$alkyl, or $(C_6-C_{14})$aryl,
wherein $R^w$ is absent or a $(C_1-C_{10})$alkyl, $(C_2-C_9)$heteroalkyl, $(C_6-C_{14})$aryl, or $(C_2-C_9)$heteroaryl;
vi) $R^x$ and $R^y$ are each independently a pharmaceutically acceptable end group.

In yet another embodiment, the polyamide has the structure of Formula (V):

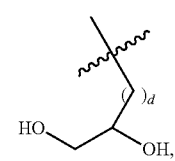

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—CH$_2$—$R_w$, $(C_1-C_{10})$alkyl, or $(C_6-C_{14})$aryl,
wherein $R^w$ is absent or a $(C_1-C_{10})$alkyl, $(C_2-C_9)$heteroalkyl, $(C_6-C_{14})$aryl, or $(C_2-C_9)$heteroaryl;
vi) $R^x$ and $R^y$ are each independently a pharmaceutically acceptable end group;
vii) $X^-$ is independently a halo or any pharmaceutically acceptable anion,
xi) $Y^1$ and $Y^2$ are each independently H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —S—O—$(C_1-C_{10})$alkyl, —O(O)C—$(C_1-C_{10})$alkyl, —$(C_1-C_{10})$alkyl-COOH, $(C_3-C_{10})$cycloalkyl-COOH, —(O)CH$_3$, —OH, amide, a dihydroxy group, represented by Formula (D), wherein d is an integer from 0 to 25, or
a polyethylene glycol group, represented by Formula (E)

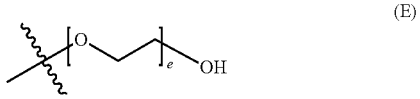

(E)

wherein e is an integer from 1 to 400.

The preservative may also include octenidine. Octenidine dihydrochloride is a cationic surfactant (at neutral or physiological pH) and bis-(dihydropyridinyl)-decane derivative, and prior to this disclosure, its primary use was as an antiseptic for topical use.

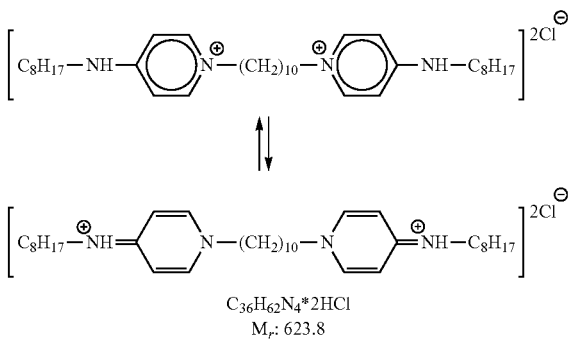

$C_{36}H_{62}N_4 * 2HCl$
$M_r$: 623.8

In another aspect, the disclosure provides methods of preparing preserved multi-dose formulations, including vaccines, using the disclosed polyamide polymers and octenidine.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

This disclosure contains no figures or drawings.

DETAILED DESCRIPTION OF THE INVENTION

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "effective amount" as used herein means an amount of a composition according to the present invention effective in producing the desired veterinary effect.

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine, canine, feline, bovine, swine, ovine, caprine, camelids, avian, primate, humans, and fish. The term "animal" also includes an individual animal in any stage of development, including embryonic and fetal stages. As used herein, the term "pig" or "piglet" means an animal of porcine origin, while "sow" refers to a female of reproductive age and capability.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an antigen, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or lowered pathogen loads in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, subunits (proteins/antigens), DNA plasmids, or a mixture thereof.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, high pressure, chemical treatment (for example, treatment with thimerosal, formalin, (betapropiolactone), BEI (binary ethylenimine)), or any other chemical agent, including octenidine, sonication, radiation, heat or any other convention means sufficient to prevent replication or growth of the organism while maintaining its immunogenicity.

Preservatives are commonly used in multi-dose formulations, including animal vaccines, to prevent bacterial or fungal growth in field conditions and are employed to minimize contamination of the formulations during repeated (non-sterile) punctures into the vial. Preservatives must pass antimicrobial effectiveness testing (AET), as described in the US pharmacopeia. As disclosed herein, Applicants performed the antimicrobial tests according to United States Pharmacopeia (USP), British Pharmacopeia (BP), and European Pharmocopeia (EP). Four test organisms were used: *Candida albicans, Pseudomonas aeruginosa, Staphylococcus aureus*, and *A. brasiliensis*. And while thimerosal and formol continue to play an important role in veterinary vaccines, European authorities encourage the development of vaccines that are free from those compounds. To overcome potential future threats linked to a potential ban, Applicants have identified two compounds and tested and confirmed the efficacy of those as WFI solutions at different concentrations for antimicrobial preservative testing according to Pharmacopoeia. As disclosed herein, both the antimicrobial polyamide polymers and octenidine are safe and effective vaccine preservatives and bacterial inactivation agents.

In one aspect of the invention, vaccine preservative compositions are provided, which comprise water soluble, antimicrobial, amine functional polyamides or octenidine. The antimicrobial polyamide may be any polyamide represented by Formula I, II, III, IV, or V. In a particular embodiment, the polyamide is selected from one of the twenty-five polymers (A-Y) listed in Table 1. In addition to the particularly effective antimicrobial polyamide species presented here, a skilled person can identify additional active members of the disclosed genus with the application of non-routine experimentation.

As illustrated in the Examples below, polyamides B and C are particularly effective against a wide range of typical contaminating pathogens, including *S. aureus, P. aeruginosa, C. albicans,* and *A. brasiliensis.* mastitis-causing pathogens, at USP and veterinarily acceptable levels.

Importantly, the values for "MW" in Table 1 indicate the "weight average molecular weight," determined by size exclusion chromatography (SEC), which is aqueous version of GPC. As such, as used herein, for example, "polymer B" is intended to encompass compositions containing polymer B having a weight average MW of about 5 to about 15 kDa, about 5 to about 12 kDa, about 5 to about 10 kDa, about 6 to about 8.5 kDa, about 7.5 to about 8 kDa, or about 7.76 kDa. Moreover, "MW" is intended to mean "weight average molecular weight," unless otherwise expressly stated.

As indicated in Table 1, polymers B, C, and D each have the same repeating structure (defined herein as poly(4,4-trimethylene dipiperidine bispropanoic acid-diaminopropane)), but a different weight average MW. Moreover, the MIC data show that polymers B, C, and D tend to be comparably effective against the panel of pathogens. Thus, Applicant has shown a wide range of poly(4,4-trimethylene dipiperidine bispropanoic acid-diaminopropane) MW grades are active antimicrobial agents (i.e. MW grades from at least about 2.5 g/mol to at least about 10.6 g/mL).

As used herein, the polymers contain the following repeating units: A [4,4-trimethylene dipiperidine bispropanoic acid-4,4'-dipiperidine]; B-D [4,4-trimethylene dipiperidine bispropanoic acid-diaminopropane]; E [2,2'-bipyrrolidine bispropanoic acid-penta diamine]; G [4,4-trimethylene dipiperidine bispropanoic acid-diaminopropane]; H [4,4-trimethylene dipiperidine bispropanoic acid-N(2-aminoethyl)-diaminoethane]; I [4,4'-trimethylene dipiperidine bispropanoic acid-N(3-aminopropyl)1,3-propane diamine]; J [4,4'-trimethylene dipiperidine bispropanoic acid-3,3'-diamino-N-methyl-dipropylamine; K [4,4'-dipiperidine bispropanoic acid-2,2'-diamino diethylamine]; L [4,4'-dipiperidine bispropanoic acid-2,2'-diamino N-methyl diethylamine]; M [4,4'-dipiperidine bispropanoic acid-3,3'-diamino-dipropylamine]; N [4,4'-dipiperidine bispropanoic acid-3,3'-diamino-N-methyl-dipropylamine]; O [4,4'-trimethylene dipiperidine-1,3-diamminopropane-N,N'-di-3-propionic acid]; P [4,4'-trimethylene dipiperidine bispropanoic acid-N,N'-dimethyl-1,3-diaminopropane]; R [4,4-trimethylene dipiperidine bispropanoic acid-4,4'-dipiperidine]; S [4,4-trimethylene dipiperidine bispropanoic acid-diaminopropane]; and T [4,4'-trimethylene dipiperidine bispropanoic acid-N-glycidol diethylene triamine].

In another aspect, the invention broadly provides multi-dose formulations comprising active pharmaceutical ingredients (API), including small molecule drugs (e.g. including famotidine), and including biologicals (e.g. peptides, including insulin). Like multi-dose vaccine formulations, multi-dose formulations containing API are subjected to contamination or inoculation with microorganisms upon repeated needle punctures. As such, in some embodiments, the invention provides preserved multi-dose API-containing formulations. API routinely included in preservative-containing, multi-dose formulations encompass, but are not limited to, the following:

Biologic therapeutics: Antivenin (*Micrurus fulvius*) (Equine Origin), Antivenin (*Crotalidae*) (Equine Origin), Antivenin (*Latrodectus mactans*), Calcitonin-salmon injection, Desmopressin acetate, Etanercept, Epoetin alfa (recombinant), Epoetin alfa (recombinant), Follitropin alfa injection, Insulin aspart (recombinant), 70% insulin aspart protamine suspension, 30% insulin aspart injection (rDNA origin), Insulin glargine [rDNA origin] injection, Insulin glulisine (rDNA origin) injection, Regular U-500 (Concentrated) (insulin human injection USP [rDNA] origin), Insulin Lispro Injection (rDNA origin), 75% Insulin Lispro Protamine Suspension and 25% Insulin Lispro Injection (rDNA origin), Interferon alfa-n3 (human leukocyte derived), Interferon alfa-2b, recombinant, Interferon alfa-2a, recombinant, Leuprolide acetate injection, Octreotide acetate injection, peginterferon alfa-2a, Rho (D) Immune Globulin (human), Rho (D) Immune Globulin (human), Sargramostim (recombinant), Somatropin (rDNA origin), Trastuzumab and Tuberculin purified protein derivative.

Vaccines: LEPTODOG®, RECOMBITEK® (inactivated vaccine against canine leptospirosis), rabies vaccines, including ALURABIFFA® and RABISIN® (inactivated rabies vaccines adjuvanted), SYNTOXAN® line (clostridia vaccine), HYORESP® (inactivated vaccine for pigs against *mycoplasma hyopneumoniae*), CIRCOVAC® (inactivated vaccine against porcine circovirus 2 (PCV2)), PARVORUVAX® (combo vaccine against porcine parvovirus, reovirus and erysipelothrix), Avian killed vaccines (for chicken & turkeys): BIGOPEST®, BINEWVAX®, COR2®, GUMBOPEST®, GUMBORIFFA®, IMOPEST®, TUR3®, FLUVAC®, GALLIMUNE® range for Breeder/Layer/Broiler: vaccines against Newcastle Disease (ND), (IBD) Infectious bronchitis, Flu H9N2, Flu H5N9, (EDS) egg drop syndrom, Swollen head syndrome, REOvirus, (ART) avian rhinotracheitis, (IB) infectious Bursal disease, Diphtheria and tetanus toxoids and acellular pertussis adsorbed, Diphtheria and tetanus toxoids and acellular pertussis adsorbed, hepatitis B (recombinant) and inactivated poliovirus vaccine combined, Diphtheria and tetanus toxoids and acellular pertussis vaccine adsorbed, Hepatitis A vaccine, inactivated, Hepatitis A inactivated and hepatitis B (recombinant) vaccine, Hepatitis B vaccine (recombinant) and Pneumococcal vaccine polyvalent.

Small molecules: Apomorphine hydrochloride injection, Enalaprilat, Enoxaparin sodium injection Intravenous (conjugated estrogens, USP) for injection, Famotidine, Fulvestrant injection, Haloperidol, Hydrocortisone sodium phosphate Hydrocortone Phosphate Injection, Hydromorphone hydrochloride, Metaraminol bitartrate, Nalbuphine hydrochloride, Methylprednisolone acetate injectable suspension, USP, Ondansetron hydrochloride, Penicillin G benzanthine suspension, Phytonadione, Sodium ferric gluconate complex in sucrose injection, Testosterone Enanthate Injection USP, Multiple Dose Vial, Medroxyprogesterone acetate injectable suspension, USP, Medroxyprogesterone acetate and estradiol cypionate injectable suspension, Flumazenil injection, Dolasetron mesylate injection and Cimetidine hydrochloride injection, Streptomycin sulfate, USP.

The present invention thus provides novel and non-obvious antimicrobial polyamide compositions, and methods of using same for treating and preventing mastitis in non-human animals. The methods generally comprise administering to an infected animal an effective amount of the veterinary composition to eliminate or cure, completely or substantially, mastitis-causing pathogen(s). As detailed below, the polyamide compounds are also highly active against a broad range of other, significant, human and animal pathogens. Moreover, the polyamides have been shown to be well-tolerated in mice and rats. For example, the maximum tolerated dose for 4,4'-trimethylene dipiperidine bispropanoic acid-co-1,3-diamino propane was about 5 mg/kg (IP) and 40 mg/kg (IV).

TABLE 1

Twenty-five Antimicrobial Amine Functional Polyamides. "MW" = weight average molecular weights

| ID # | Structure | MW (kDa) |
|---|---|---|
| A | 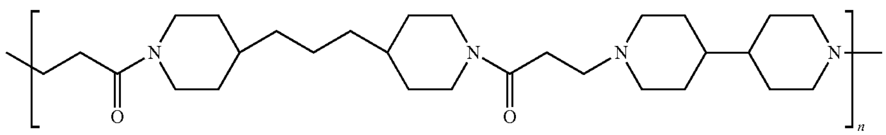 | 10.6 |
| B | 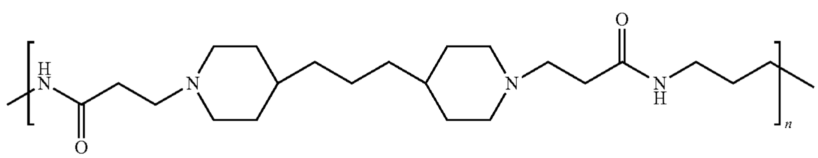 | 7.76 |
| C | 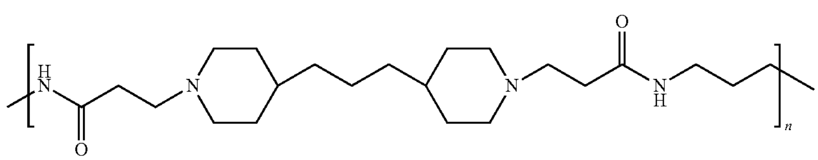 | 3.35 |
| D | 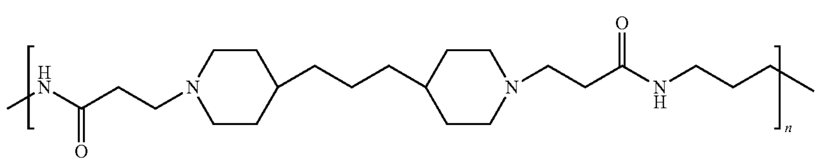 | 2.5 |
| E | 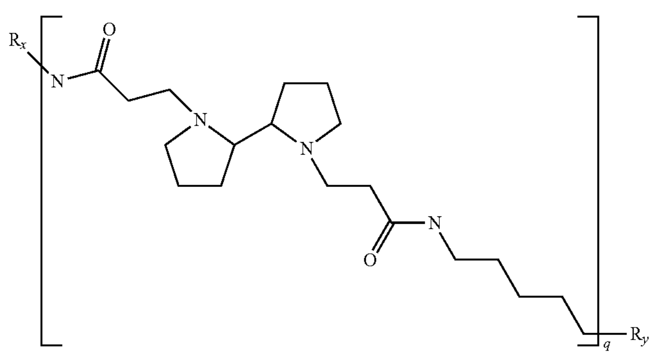 | 3.0 |
| F | 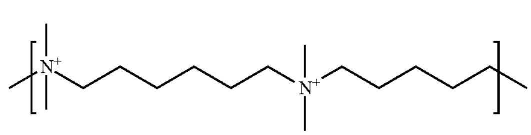 | 4.2 |
| G | 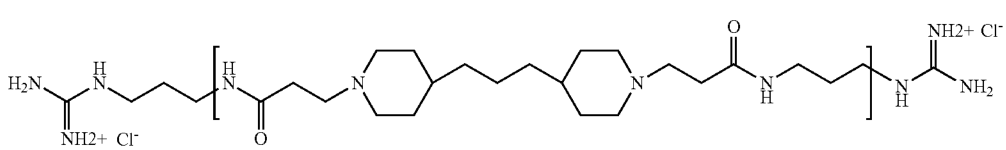 | 2.0 |

TABLE 1-continued
Twenty-five Antimicrobial Amine Functional Polyamides. "MW" = weight average molecular weights
| ID # | Structure | MW (kDa) |
|---|---|---|
| H | 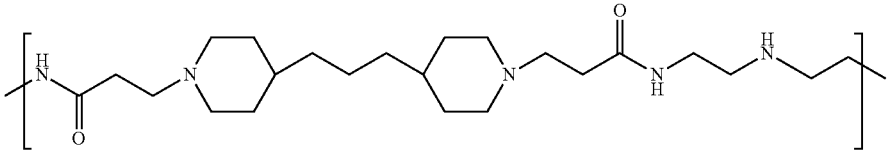 | 3-10 |
| I | 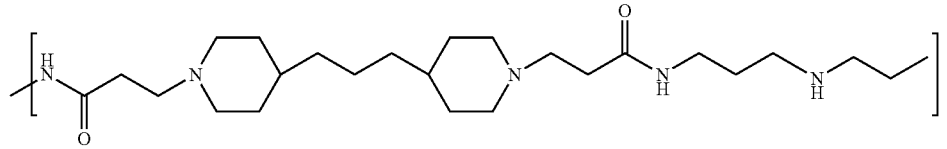 | 5.0 |
| J | 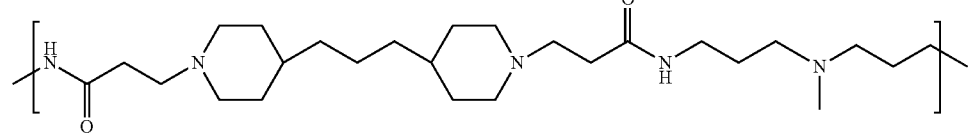 | 5.0 |
| K | 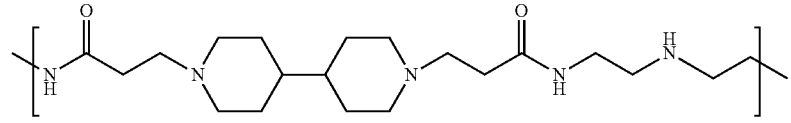 | 7.0 |
| L | 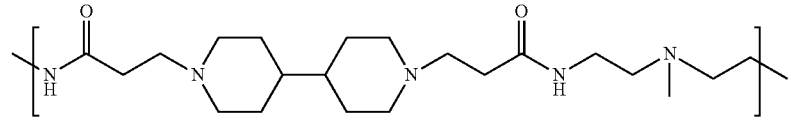 | 5.0 |
| M | 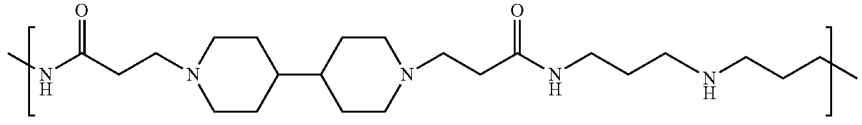 | 5.4 |
| N | 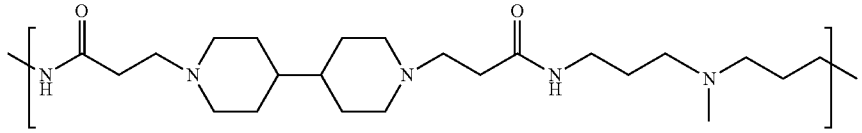 | 5.5 |
| O | 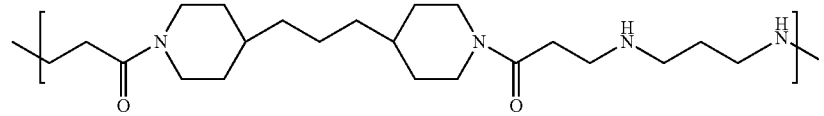 | 10.0 |
| P | 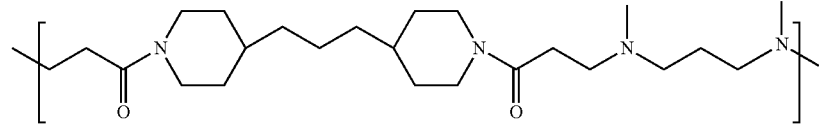 | 5.4 |
| Q | 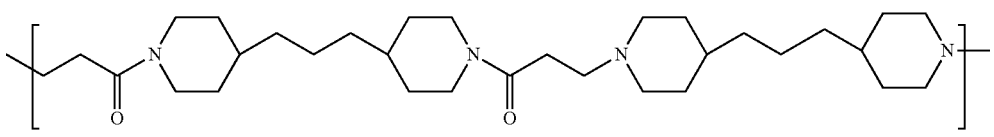 | 7.5 |

TABLE 1-continued

Twenty-five Antimicrobial Amine Functional Polyamides. "MW" = weight average molecular weights

| ID # | Structure | MW (kDa) |
|---|---|---|
| R | 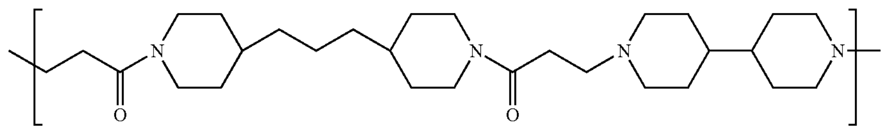 | 3-10 |
| S | 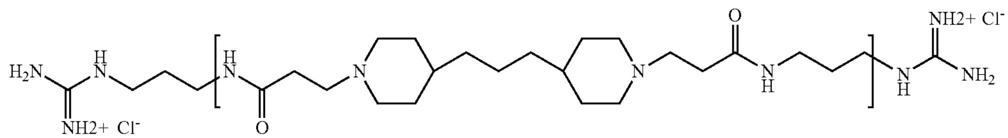 | 4.9 |
| T | 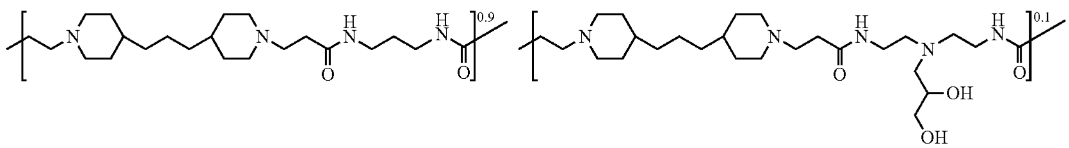 | 4.5 |
| U | | ~10 |
| V | 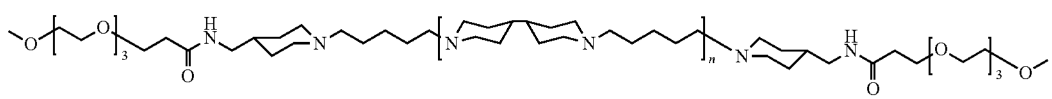 | 8.4 |
| W | | ~10 |
| X | | 5-10 |
| Y | | 5-10 |

"Substituted" means the substitution of a carbon in alkyl, heterocyclic or aryl groups with one or more non-carbon substituent. Non-carbon substituents are selected from nitrogen, oxygen and sulfur.

"Unsubstituted" means the group is comprised of only hydrogen and carbon.

The term "polymer" means a molecule comprised of repeating units. The term "repeat unit" or "monomer" means a group in a polymer that repeats or appears multiple times in a polymer. A polymer may be a copolymer if the repeating units or "comonomers" are chemically and structurally different from one another.

The term "pharmaceutically acceptable anion" means an anion that is suitable for pharmaceutical use. Pharmaceutically acceptable anions include but are not limited to halides, carbonate, bicarbonate, sulfate, bisulfate, hydroxide, nitrate, chloride, phosphate, persulfate, sulfite, acetate, ascorbate, benzoate, citrate, dihydrogen citrate, hydrogen citrate, oxalate, succinate, tartrate, taurocholate, glycocholate, and cholate.

The term "pharmaceutically acceptable end group" means an end group that is suitable for pharmaceutical use. Examples of pharmaceutically acceptable end groups include but are not limited to H, $(C_1-C_{10})$alkyl, $(C_2-C_9)$ heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —O(O)C—$(C_1-C_{10})$alkyl, $(C_1-C_{10})$alkyl-COOH, $(C_3-C_{10})$ cycloalkyl-COOH, —(O)CH$_3$, —OH, amide, a guanidino group, a guanidinium chloride group, a guanidinobenzene group, a dihydroxy group, and a polyethylene glycol group.

The term "effective amount" of a disclosed amine functional polyamides is a quantity sufficient to achieve a therapeutic and/or prophylactic effect on the particular condition being treated, such as an amount which results in the prevention or a decrease in the symptoms associated with mastitis. The precise amount of the disclosed amine functional polyamides that is administered will depend on the type and severity of mastitis or infection being treated and on the characteristics of the animal, such as general health, age, body weight and tolerance to drugs.

In one embodiment of the method, an effective amount of the polyamide or octenidine is added to one or more antigens to form a stable immunological composition.

According to another aspect of the present invention, a use of an antimicrobial amine functional polyamide for preserving a vaccine formulation is provided.

Preserved Vaccine Compositions

In accordance with the present invention, the preserved vaccine composition comprises a water soluble, antimicrobial polyamide polymer. Particularly effective polyamides include polymers B, C, D, U, and T.

As used herein, the term "preserving effective amount" refers to a concentration of preservative sufficient to prevent the growth of contaminating microorganisms in a multiuse vaccine formulation.

The preservative-containing immunogenic composition of the present invention may be resistant to several pathogens including *E. coli, Klebsiella* spp., *Enterobacter* spp., *Salmonella* spp., *Citrobacter* spp., *Serratia* spp., *Shigella* spp., *Edwardsiella* spp., *Hafnia* spp., *Morganella* spp., *Providencia* spp., *Yersinia* spp., *Staphylococcus aureus, Staphylococcus* spp., *Pseudomonas* spp., *Streptococcus agalactiae, Streptococcus dysgalactiae, Streptococcus* spp., *Enterococci, Corynebacterium* spp., *Arcanobacterium* spp., *Actinomyces* spp., *Mycobacterium* spp., *Prototheca* spp., *Mycoplasma* spp., *Erwinia* spp., *Lactobacillus* spp., among others.

In an embodiment, the preservative-containing composition comprises a *Borrelia burgdorferi* bacterial extract (e.g. antigens disclosed in any of U.S. Pat. Nos. 5,523,089, 5,582,990, 5,688,512, 5,777,095 and 6,083,722, each to Symbicom). In one embodiment, the antigen comprises an expression vector containing OspA (e.g. as disclosed in U.S. Pat. No. 6,159,477 or 6,368,603, both to Merial).

In another embodiment, the preservative-containing multi-dose formulation comprises an *E. Coli* bacterin-toxoid (e.g. Merial's J-VAC®). In other embodiments, multi-dose formulation comprises one or more of the antigens in the following vaccine compositions: LEPTODOG®, RECOMBITEK® (inactivated vaccine against canine leptospirosis), rabies vaccines, including ALURABIFFA® and RABISIN® (inactivated rabies vaccines adjuvanted), SYNTOXAN® line (clostridia vaccine), HYORESP® (inactivated vaccine for pigs against *mycoplasma hyopneumoniae*), CIRCOVAC® (inactivated vaccine against porcine circovirus 2 (PCV2)), PARVORUVAX® (combo vaccine against porcine parvovirus, reovirus and erysipelothrix), Avian killed vaccines (for chicken & turkeys): BIGOPEST®, BINEWVAX®, COR2®, GUMBOPEST®, GUMBORIFFA®, IMOPEST®, TUR3®, FLUVAC®, GALLIMUNE® range for Breeder/Layer/Broiler: vaccines against Newcastle Disease (ND), (IBD) Infectious bronchitis, Flu H9N2, Flu H5N9, (EDS) egg drop syndrom, Swollen head syndrome, REOvirus, (ART) avian rhinotracheitis, (IB) infectious Bursal disease, In an embodiment, the composition is a multi-dose vaccine composition. In some embodiments, the multi-dose vaccine composition is a monovalent compositions. In other embodiments, the multi-dose vaccine composition is a multi-valent vaccine composition.

In embodiments where the multi-dose composition is a monovalent composition, the antigen may include one antigen, including one selected from an antigen present in one of the following vaccines: LEPTODOG®, RECOMBITEK® (inactivated vaccine against canine leptospirosis), rabies vaccines, including ALURABIFFA® and RABISIN® (inactivated rabies vaccines adjuvanted), SYNTOXAN® line (clostridia vaccine), HYORESP® (inactivated vaccine for pigs against *mycoplasma hyopneumoniae*), CIRCOVAC® (inactivated vaccine against porcine circovirus 2 (PCV2)), and PARVORUVAX® (combo vaccine against porcine parvovirus, reovirus and erysipelothrix).

In embodiments where the multi-dose composition is a multivalent composition, the composition contains at least two antigens, including antigens selected from among the following: canarypox-vectored canine distemper, adenovirus type 2, parainfluenza, parvovirus (MLV), Leptospira Canicola bacterin and Leptospira icterohaemorrhagiae Bacterin (e.g. Merial's RECOMBITEK® C6). In another embodiment, the multi-valent composition contains: Encephalomyelitis-Influenza Vaccine, Eastern and Western, Killed Virus, Tetanus Toxoid (i.e. Merial's EQUINE EWTF).

In view of the above, it will be seen that the several objects of the invention are achieved and other advantageous results attained. As various changes could be made in the above formulations, products, and processes without departing from the scope of the invention, it is intended that all matter contained in the above description and shown in the accompanying tables shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. Moreover, the term "consisting essentially of" is intended to mean that there may be additional elements other than the listed elements, but not ones that would be considered "active ingredients" (e.g. non-active excipients). And finally, the term "consisting of" is intended to mean that only the listed elements are included.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In one aspect, the invention provides a method of preserving a multi-dose formulation, including those containing therapeutic biologics, vaccines, and small molecules, comprising mixing the multi-dose formulations with a non-mercurial preservative, selected from a polyamide polymer and octenidine, to form a preserved multi-dose formulation, thereby preserving the multi-dose formulation.

In some embodiments, the invention provides a method of preparing a preserved multi-dose formulation, the method comprising, consisting essentially of, or consisting of the following steps: a) providing at least two effective doses of one or more active pharmaceutical ingredient (API); b) providing a preservative effective amount of a non-mercurial preservative selected from one or more antimicrobial polyamide polymer(s), octenidine and combinations thereof; c) combining the API and the non-mercurial preservative with an aqueous and/or oily component to form a preserved multi-dose liquid formulation; d) optionally providing one or more excipient; e) optionally providing a container for containing the liquid formulation; f) optionally sterilizing and transferring the liquid formulation to the container; and g) optionally freeze-drying, lyophilizing and/or vitrifying the liquid formulation; thereby producing the preserved multi-dose formulation; and wherein the formulation contains no mercurial preservative.

The foregoing steps may be practiced in any reasonable order. For example, the non-mercurial preservative(s), API (s) and optional excipient may be placed into a mixing vessel containing an aqueous and/or oily component. Once thoroughly mixed into a solution, suspension, suspoemulsion, emulsion or micellar solution, the preserved liquid formulation may then be filter-sterilized and aseptically transferred into sterile containers, including vaccine vials. The excipient may include any pharmaceutically or veterinarily acceptable excipient, including those that improve the solubility of the non-mercurial preservative(s). Moreover, any suitable preserved liquid formulation may be produced.

In particular embodiments, the liquid formulation may be an aqueous solution, a micellar solution, a swollen micellar solution, an oil-in-water emulsion, a water-in-oil emulsion or a suspoemulsion. In general, for preserved immunological or other biologic formulations, the antigen or other biologic is dissolved within the aqueous phase of a multi-phasic liquid formulation. The emulsions may be microemulsions or "submicron" emulsions. Submicron emulsions are generally referred to herein as "nanoemulsions."

Moreover, for the preservative to be deemed to be present in the preserved multi-dose formulations in a "preservative effective amount," the formulations should be protected from inoculation with micro-organisms as disclosed herein. For example, if the amount of bacteria inoculated into a preserved multi-dose formulation decreases over time, the non-mercurial preservative is deemed to be present in a preservative effective amount. In another example, the preservative is present in a preservative effective amount when the preserved formulation passes the tests detailed in Examples 1, 2 and/or 3.

In another aspect, the invention provides a preserved multi-dose formulation, wherein: a) the formulation comprises at least two effective doses of one or more active pharmaceutical ingredient (API) and a preservative effective amount of a non-mercurial preservative selected from one or more antimicrobial polyamide polymer(s), octenidine and combinations thereof; or b) the formulation is produced according to the disclosed method of preparing a preserved multi-dose formulation; and wherein the formulation contains no mercurial preservative.

In some embodiments, the preserved multi-dose formulation comprises a polyamide polymer selected from:

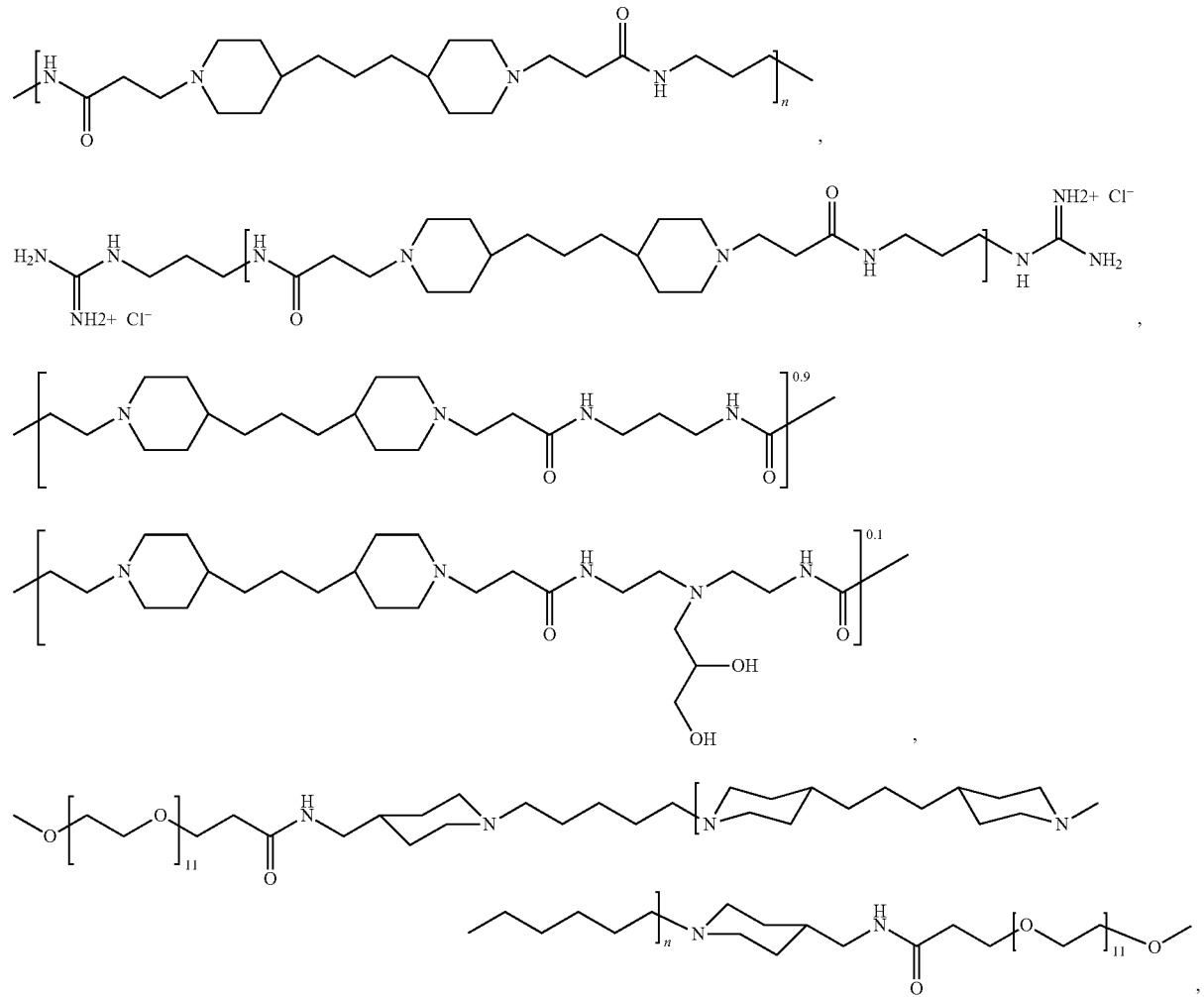

and combinations thereof.

In some embodiments, the preserved multi-dose formulation comprises a polyamide polymer having the following structure:

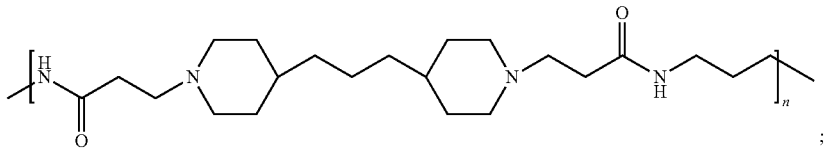

and wherein the weight average molecular weight (WAMW) is from about 1.0 kDa to about 15.0 kDa, as measured by size exclusion chromatography. In other embodiments, the polyamide may have a WAMW from about 2.0 kDa to about 10 kDa. In still other embodiments, the polyamide may have a WAMW from about 2.5 kDa to about 7.76 kDa, or has a WAMW of about 7.76 kDa.

In another aspect, the invention provides an immunogenic composition comprising at least one antigen, and further comprising at least about 0.01 mg/mL of polyamide polymer or at least about 0.1 mg/mL octenidine. In the immunogenic composition, the polyamide polymer or octenidine may be present at a concentration of between about 0.05 mg/mL to about 5 mg/mL or between about 0.1 mg/mL to about 0.25 mg/mL. In some embodiments, the polyamide polymer or octenidine is present at a concentration of about 0.1 mg/mL, about 0.125 mg/mL or about 0.25 mg/mL. Now that the invention has been disclosed, the skilled person may make routine adjustments to the concentrations of these safe and effective non-mercurial preservatives to achieve the desired preservative efficacy.

In still other embodiments, the immunogenic composition comprises not less than about 0.1 mg/mL of the polyamide polymer. In some embodiments, the composition comprises not less than about 0.1 mg/mL of the octenidine.

In some embodiments, the immunogenic composition further comprises an adjuvant. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin (including from the bark of *Quillaja saponaria*), (8) other adjuvants discussed in any document cited and incorporated by reference into the instant application, or (9) any combinations or mixtures thereof.

The oil-in-water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of cross linked acrylic or methacrylic acid, especially cross linked by polyalkenyl ethers of sugars or polyalcohols. These compounds are known under the name carbomer (Pharmeuropa, vol. 8, no. 2, Jun. 1996). One skilled in the art can also refer to U.S. Pat. No. 2,909,462, which provides such acrylic polymers cross linked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are cross linked by allyl saccharose or by allyl pentaerythritol. Among them, reference is made to Carbopol 974P, 934P and 971P.

In some embodiments, the antigenicity of the immunogenic composition is stable for not less than 1 year, 1.5 years, 2 years or 2.5 years.

In other embodiments, following inoculation of the immunogenic composition (or other preserved formulation) with one or more micro-organisms, the concentration of said micro-organisms is reduced over time owing to the presence of the preservative. When this reduction is observed, the non-mercurial preservative is deemed to be present in a "preservative effective amount."

In some embodiments, following inoculation with one or more bacteria strains, the immunogenic composition (or other preserved formulation) presents at least 1.0 log reduction from the initial micro-organism count at 24 hours, at least 3.0 log reduction at 7 days from the previous value measured and not more than 0.5 log increase at 28 days from the previous value measured.

In still other embodiments, following inoculation with one or more bacteria strains, the immunogenic composition (or other preserved formulation) presents at least 2.0 log reduction from the initial calculated count at 6 hours after inoculation, at least 3.0 log reduction at 24 hours from the previous value measured and no recovery at 28 days.

In some embodiments, the one or more micro-organisms are selected from *P. aeruginosa*, *S. aureus*, *E. coli* and *B. subtilis*.

In other embodiments, the immunogenic composition (or other preserved formulation) is inoculated multiple times. For example, a second inoculation may occur at 6 hours following an initial inoculation, a third inoculation may occur at 24 hours following the initial inoculation, a fourth inoculation may occur at 7 days following the initial inoculation and a fifth inoculation may occur at 14 days following the initial inoculation.

In some embodiments, the immunogenic composition (or other preserved formulation) may further comprise one or more of a buffer, a cryoprotectant, a salt, a divalent cation, a non-ionic detergent, and an inhibitor of free radical oxidation.

In another aspect, the invention provides a vial containing an immunogenic composition (or other preserved formulation) as disclosed herein.

In some embodiments, the vial may contain more than two doses of the immunogenic composition (or other preserved formulation).

In another aspect, the disclosure provides a preserved multi-dose formulation made according to the disclosed methods.

In another aspect, the disclosure provides an immunogenic composition comprising at least one antigen, and at least about 0.01 mg/mL to about 0.25 mg/mL of the polyamide polymer or at least about 0.1 mg/mL to about 1.0 mg/mL octenidine.

In some embodiments, the immunogenic composition (or other preserved formulation) comprises between about 0.05 mg/mL and about 5 mg/mL, or between about 0.1 mg/mL and about 0.25 mg/mL of the polyamide polymer or the octenidine.

In some embodiments, the immunogenic composition (or other preserved formulation) comprises between about 0.1 mg/mL and about 0.25 mg/mL of the polyamide polymer or the octenidine.

In other embodiments, the immunogenic composition (or other preserved formulation) comprises not less than about 0.1 mg/mL of the polyamide polymer.

In still other embodiments, the immunogenic composition (or other preserved formulation) comprises not less than about 0.1 mg/mL of the octenidine.

In some embodiments, buffered solutions containing relatively lower amounts of salts, particularly including phosphate salts, are added to the immunogenic composition, or other preserved multi-dose formulation, to improve the solubility of the octenidine. This is based on Applicants' unexpected discovery that octenidine is less soluble in routinely used phosphate buffered saline (PBS). To address the problem of poor solubility, Applicants' tried a variety of modifications and, ultimately determined that replacing the sodium phosphate with sodium bicarbonate provided the required solubility. As such, in some embodiments, multi-dose formulations including octenidine contain less phosphate than standard PBS. Accordingly, in some embodiments, the buffer may contain for 100 L about 5 g of $NaH_2PO_4$ and about 200 g of Sodium bicarbonate (instead of standard PBS, which contains about a 20:1 ratio of $Na_2HPO_4$ to $KH_2PO_4$).

In some embodiments, the buffer may contain relatively less NaCl, with osmolality maintained by the compensatory addition of an appropriate amount of glucose. The buffer may be further supplemented with additional divalent ions, $CaCL_2$ and MgC12.

In some embodiments, the quantity of phosphate is generally reduced 50-fold, as compared to standard PBS, with bicarbonate substituting for the phosphate.

In some embodiments, the immunogenic composition comprises an adjuvant.

In an embodiment of the immunogenic composition, the antigenicity of the immunogenic composition is stable for not less than 1 year, 1.5 years, 2 years or 2.5 years.

In general, a "stable" multi-dose formulation exhibits no unacceptable levels of microbial growth, and substantially no or no breakdown or degradation of the active biological or small molecule component. As used herein, a "stable immunogenic composition" is a preserved formulation that remains capable of eliciting a desired immunologic response when administered to a target animal. Stable immunogenic compositions often include those that lose no more than one half of a log of activity during some specified time interval. For example, "stable for at least one year" means that an immunogenic composition with a beginning titer of about X Log 10 CCID50/dose of activity will retain at least about (X-0.5) Log 10 CCID50/dose of activity for at least one year after the preserved immunogenic composition has been prepared (e.g. placed into its sterile container; or, resuspended from a freeze-dried pastille contained within a sterile vial).

In particular embodiments, the preserved multi-use formulations, including preserved immunogenic compositions, remain stable for the specified time with numerous repeated inoculations/insertions into the multi-dose containers. In such cases, a term such as "stable for at least one year with up to ten usages" may be used to described a preserved formulation, which is contained within a multi-dose container. In some preferred embodiments, the multi-dose formulations remain stable even with 10, 15, 20, 30, 40, 50 or even 100 inoculations/insertions.

In an embodiment, following inoculation of the immunogenic composition with one or more micro-organisms, the concentration of said micro-organisms is reduced over time. As used herein, "inoculation of the composition" refers generally to the introduction into the composition of a foreign object (e.g. an hypodermic needle), which may contain potentially contaminating microorganisms. An example of inoculation is the repeated introduction of needles into a vial containing a multi-dose vaccine formulation. Another example is the repeated introduction of needles into a vial containing a multi-dose vaccine formulation. Each of the foregoing are examples of "inoculation," as used herein.

In some embodiments, following inoculation of the immunogenic composition with one or more bacteria strains, the composition presents at least 1.0 log reduction from the initial micro-organism count at 24 hours, at least 3.0 log reduction at 7 days from the previous value measured and not more than 0.5 log increase at 28 days from the previous value measured.

In other embodiments, following inoculation of the immunogenic composition, the composition presents at least 2.0 log reduction from the initial calculated count at 6 hours after inoculation, at least 3.0 log reduction at 24 hours from the previous value measured and no recovery at 28 days. In some embodiments, the one or more micro-organisms are selected from the group consisting of *P. aeruginosa, S. aureus, E. coli* and *B. subtilis*.

In some embodiments, the composition is inoculated multiple times, including 2, 3, 4, 5, 6, 7, 8, 9, 10, 11, 12, 13, 14, 15, 16, 17, 18, 19, 20 or more times. Any number of inoculations above 1 are envisioned by Applicants.

In some embodiments, a second inoculation occurs at 6 hours following an initial inoculation, a third inoculation occurs at 24 hours following the initial inoculation, a fourth inoculation occurs at 7 days following the initial inoculation and a fifth inoculation occurs at 14 days following the initial inoculation.

In other embodiments, the immunogenic composition comprises one or more of a buffer, a cryoprotectant, a salt, a divalent cation, a non-ionic detergent, and an inhibitor of free radical oxidation.

In an embodiment, the disclosure provides a vial containing the multi-dose immunogenic or other active-containing composition.

In an embodiment, the vial contains more than 1, 2, 3, 4, 5, 6, 7, 8, 9, 10, 11, 12, 13, 14, 15, 16, 17, 18, 19 or 20 doses of the immunogenic composition.

In an embodiment, the disclosure provides a pre-filled vaccine delivery device comprising a multi-dose formulation comprising biologic or small molecule active ingredients. In some embodiments, the device comprises a syringe. In other embodiments, the device comprises a dual or multiple chamber syringe or vials or combinations thereof. In yet other embodiments, the pre-filled vaccine delivery device comprises a multivalent immunogenic composition that is formulated for intramuscular or subcutaneous injection.

In an embodiment, the container comprises two doses or more of the multivalent immunogenic composition of claim 7, wherein each dose comprises 0.1 to 2 mL of the composition. In some embodiments, the composition comprises polyamide polymer at a concentration of between about 0.1 mg/dose to about 0.25 mg/dose or between about 0.05 mg/dose and about 0.125, wherein the dose is a 0.5 mL dose.

The following examples are simply intended to further illustrate and explain the present invention. The examples, therefore, should not be regarded as limiting the scope of the invention or manner in which it may be practiced.

EXAMPLES

As described below, both the antimicrobial polyamide polymers and octenidine were tested and demonstrated to be effective vaccine privative agents. Table 2 presents a comparison of USP and EP requirements for antimicrobial effectiveness testing for vaccine preservative agents.

TABLE 2

USP and EP requirement for antimicrobial effectiveness testing

| Time | USP | EP A | EP B |
|---|---|---|---|
| Requirements for bacterial log reduction ||||
| 6 h | Not required | 2 | Not required |
| 24 h | Not required | 3 | 1 |
| 7 d | 1 | No recovery | 3 |
| 14 d | 3 | No recovery | No increase |
| 28 d | No increase | No recovery | No increase |
| Requirements for fungal log reduction ||||
| 7 d | No increase | 2 | No increase |
| 14 d | No increase | No increase | 1 |
| 28 d | No increase | No increase | No increase |

Meyer B. K. "Antimicrobial Preservative Use in Parenteral Products: Past and Present," Merck Research Laboratories. J. of Pharmaceutical Sciences, 2007

Tables 3 and 4 present the acceptance criteria/European Pharmacopoeia (§ 5.1.3) and European Pharmacopoeia for vaccine for veterinary use.

TABLE 3

Acceptance criteria/European Pharmacopoeia (Sec. 5.1.3)

|  | 6 h | 24 h | 7 days | 14 days | 28 days |
|---|---|---|---|---|---|
| Bacteria | 2 log | 3 log | — | — | NR |
|  | — | 1 log | 3 log | — | NI |
| Fungi | — | — | 2 log | — | NI |
|  | — | — | — | 1 log | NI |

NR: No recovery
NI: No increase in number of viable micro-organisms compared to the previous reading

TABLE 4

Acceptance criteria/European Pharmacopoeia for vaccines for veterinary use

|  | 24 h 7 days | 14 days | 28 days |
|---|---|---|---|
| Bacteria | NI | 3 log | NI |
| Fungi | — | NI | NI |

NI: No increase in number of viable micro-organisms compared to the previous reading

Example 1

Polyamide Preservative Study

Meyer et al. (J. Pharm. Sc. 96(12):3155-67; 2007) indicated the following Minimum Inhibitory Concentration (MIC) data for thimerosal: 4-8 µg/mL (*E. coli, Pseudomonas aeruginosa*); 0.2 µg/mL (*Staphylococcus aureus*); 32 µg/mL (*Candida albicans*); 128 µg/mL (*Aspergillus niger*). Further, the concentration of thimerosal in various Merial veterinary vaccines is about 0.005% to about 0.01% (=about 50 to about 100 µg/ml). Based on the foregoing, three different doses of the polyamide polymer were selected as a starting point (0.1, 1 and 10 mg/mL). Applicants could not predict in advance whether these concentrations would be effective.

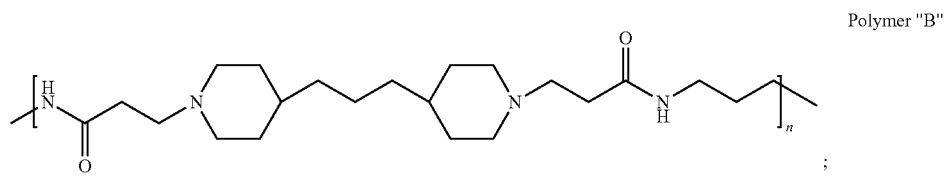

Polymer "B"

MW=7.6 kDa (see Table 1)

TABLE 5

Preservative efficacy of polyamide polymer
(A and B are criteria from the European pharmacopeia)

|  | S. aureus | | | P. aeruginosa | | | C. albicans | | | A. brasiliensis | | |
|---|---|---|---|---|---|---|---|---|---|---|---|---|
|  | Dose (mg/mL) ||||||||||||
| Criteria | 0.1 | 1 | 10 | 0.1 | 1 | 10 | 0.1 | 1 | 10 | 0.1 | 1 | 10 |
| A criteria |  | + |  |  | + |  |  | + |  |  | − |  |
| B criteria |  | + |  |  | + |  |  | + |  |  | − |  |
| USP |  | + |  |  | + |  |  | + |  |  | + |  |
| Veterinary use |  | + |  |  | + |  |  | + |  |  | + |  |

Satisfactory Vet and USP were obtained with the three doses. No low-dose effect observed, indicating the optimal dose is likely less than 100 µg/mL.

Methodology.

For each concentration of polyamide polymer, dilution neutralization was carried out by inoculating 10 mL of test product with 100 µL of each test strain. Countings were performed at Do, 6 h (bacteria only), 24 h (bacteria only), D7, D14 and D28. For each counting, 1 mL of the sample was neutralized in 9 mL of neutralizing solution (10 minutes), for S. aureus, a second 1:10 dilution in the same solution. Then 1 mL of the mixture was transferred in Petri dishes and covered with 15 mL of agar medium (Trypcase Soy Agar for bacteria and Sabouraud Dextrosed Agar for yeasts and molds). The countings were achieved after 24-48 hours incubation at 32.5° C.±2.5° C. for bacteria, and 48-72 hours at 22.5° C.±25° C. for yeasts and molds. The test micro-organisms included *Staphylococcus aureus, Pseudomonas aeruginosa, Candida albicans* and *Aspergillus brasiliensis*. Finally, the neutralization solution contained: Tween 80 (10%), lecithin (2%), saponin (2%), sodium thiosulfate (0.5%) and buffered solution chloride. The saponin was from the bark of *Quillaja saponaria*.

TABLE 6

Preservative efficacy of polyamide polymer at 0.1 mg/mL
A0202-32B - 0.1 mg/mL

|  | S. aureus | | P. aeruginosa | | C. albicans | | A. brasiliensis | |
|---|---|---|---|---|---|---|---|---|
| Inoculum | $8 \times 10^6$ | | $7.9 \times 10^5$ | | $1.7 \times 10^5$ | | $1.9 \times 10^5$ | |
| T0 | $2 \times 10^3$ | | $4.9 \times 10^3$ | | $2.6 \times 10^2$ | | $4.1.0 \times 10^5$ | |
| 6 h | <10 | >5.3 log | <10 | >4.9 log | – | | – | |
| 24 h | <10 | >5.3 log | <10 | >4.9 log | – | | – | |
| 7 d | <10 | >5.3 log | <10 | >4.9 log | <10 | >4.2 log | $9.7 \times 10^4$ | 0.3 log |
| 14 d | <10 | >5.3 log | <10 | >4.9 log | <10 | >4.2 log | $1.0 \times 10^5$ | 0.3 log |
| 28 d | <10 | >5.3 log | <10 | >4.9 log | <10 | >4.2 log | $6.6 \times 10^4$ | 0.5 log |
| A Criteria | + | | + | | + | | – | |
| B Criteria | + | | + | | + | | – | |
| Veterinary Use | + | | + | | + | | + | |

TABLE 7

Preservative efficacy of polyamide polymer at 1.0 mg/mL
A0202-32B - 1.0 mg/mL

|  | S. aureus | | P. aeruginosa | | C. albicans | | A. brasiliensis | |
|---|---|---|---|---|---|---|---|---|
| Inoculum | $8 \times 10^6$ | | $7.9 \times 10^5$ | | $1.7 \times 10^5$ | | $1.9 \times 10^5$ | |
| T0 | $8 \times 10^3$ | | $4.9 \times 10^3$ | | 10 | | $3.3 \times 10^5$ | |
| 6 h | <10 | >5.3 log | <10 | >4.9 log | – | | – | |
| 24 h | <10 | >5.3 log | <10 | >4.9 log | – | | – | |
| 7 d | <10 | >5.3 log | <10 | >4.9 log | <10 | >4.2 log | $9.1 \times 10^4$ | 0.3 log |
| 14 d | <10 | >5.3 log | <10 | >4.9 log | <10 | >4.2 log | $9.6 \times 10^4$ | 0.3 log |
| 28 d | <10 | >5.3 log | <10 | >4.9 log | <10 | >4.2 log | $6.3 \times 10^4$ | 0.5 log |
| A Criteria | + | | + | | + | | – | |
| B Criteria | + | | + | | + | | – | |
| Veterinary Use | + | | + | | + | | + | |

TABLE 8

Preservative efficacy of polyamide polymer at 10 mg/mL
A0202-32B - 10 mg/mL

|  | S. aureus | | P. aeruginosa | | C. albicans | | A. brasiliensis | |
|---|---|---|---|---|---|---|---|---|
| Inoculum | $8 \times 10^6$ | | $7.9 \times 10^5$ | | $1.7 \times 10^5$ | | $1.9 \times 10^5$ | |
| T0 | $2.3 \times 10^5$ | | $3 \times 10^3$ | | $7.2 \times 10^2$ | | $3.9 \times 10^5$ | |
| 6 h | <10 | >4.3 log | <10 | >4.9 log | – | | – | |
| 24 h | <10 | >4.3 log | <10 | >4.9 log | – | | – | |
| 7 d | <10 | >4.3 log | <10 | >4.9 log | <10 | >4.2 log | $4.4 \times 10^4$ | 0.6 log |
| 14 d | <10 | >4.3 log | <10 | >4.9 log | <10 | >4.2 log | $4.4 \times 10^4$ | 0.6 log |
| 28 d | <10 | >4.3 log | <10 | >4.9 log | <10 | >4.2 log | $1.8 \times 10^4$ | 1 log |
| A Criteria | + | | + | | + | | – | |
| B Criteria | + | | + | | + | | – | |
| Veterinary Use | + | | + | | + | | + | |

Example 2

Octenidine Preservative Study

Methodology.
For each concentration of octenidine, dilution neutralization was carried out as disclosed in Example 1.

TABLE 9

Preservative efficacy of octenidine dihydrochloride (1 mg/mL)
Octenidine Dihydrochloride - 1 mg/mL

|  | S. aureus | | P. aeruginosa | | C. albicans | | A. brasiliensis | |
|---|---|---|---|---|---|---|---|---|
| Inoculum | $1.0 \times 10^6$ | | $1.2 \times 10^6$ | | $1.9 \times 10^5$ | | $1.9 \times 10^5$ | |
| T0 | $<10^2$ | | <10 | | <10 | | $1.6 \times 10^5$ | |
| 6 h | $<10^2$ | >4 log | <10 | >5.1 log | – | | – | |
| 24 h | $<10^2$ | >4 log | <10 | >5.1 log | – | | – | |
| 7 d | $<10^2$ | >4 log | <10 | >5.1 log | <10 | >4.3 log | $2.9 \times 10^4$ | 0.8 log |
| 14 d | $<10^2$ | >4 log | <10 | >5.1 log | <10 | >4.3 log | $1.7 \times 10^4$ | 1 log |
| 28 d | $<10^2$ | >4 log | <10 | >5.1 log | <10 | >4.3 log | $1.4 \times 10^4$ | 1.1 log |
| A Criteria | + | | + | | + | | – | |
| B Criteria | + | | + | | + | | + | |
| Veterinary Use | + | | + | | + | | + | |

TABLE 10

Preservative efficacy of octenidine dihydrochloride (0.1 mg/mL)
Octenidine Dihydrochloride - 0.1 mg/mL

|  | S. aureus | | P. aeruginosa | | C. albicans | | A. brasiliensis | |
|---|---|---|---|---|---|---|---|---|
| Inoculum | $1.0 \times 10^6$ | | $1.2 \times 10^6$ | | $1.9 \times 10^5$ | | $1.9 \times 10^5$ | |
| T0 | <10 | | <10 | | <10 | | $1.7 \times 10^5$ | |
| 6 h | $<10^2$ | >5 log | <10 | >5.1 log | – | | – | |
| 24 h | $<10^2$ | >5 log | <10 | >5.1 log | – | | – | |
| 7 d | $<10^2$ | >5 log | 50 | 4.4 log | <10 | >4.3 log | $7.5 \times 10^4$ | 0.4 log |
| 14 d | $<10^2$ | >5 log | <10 | >5.1 log | <10 | >4.3 log | $1.0 \times 10^4$ | 1.3 log |
| 28 d | $<10^2$ | >5 log | <10 | >5.1 log | <10 | >4.3 log | $2.8 \times 10^4$ | 0.8 log |
| A Criteria | + | | + | | + | | – | |
| B Criteria | + | | + | | + | | + | |
| Veterinary Use | + | | + | | + | | + | |

TABLE 11

Preservative efficacy of octenidine dihydrochloride (0.01 mg/mL)
Octenidine Dihydrochloride - 0.01 mg/mL

|  | S. aureus | | P. aeruginosa | | C. albicans | | A. brasiliensis | |
|---|---|---|---|---|---|---|---|---|
| Inoculum | $1.0 \times 10^6$ | | $1.2 \times 10^6$ | | $1.9 \times 10^5$ | | $1.9 \times 10^5$ | |
| T0 | 10 | | <10 | | $2 \times 10^3$ | | $2.8 \times 10^5$ | |
| 6 h | <10 | >5 log | <10 | >5.1 log | – | | – | |
| 24 h | <10 | >5 log | <10 | >5.1 log | – | | – | |
| 7 d | <10 | >5 log | <10 | 4.4 log | <10 | >4.3 log | $3.8 \times 10^4$ | 0.7 log |
| 14 d | <10 | >5 log | <10 | 4.4 log | <10 | >4.3 log | $3.2 \times 10^4$ | 0.8 log |
| 28 d | <10 | >5 log | <10 | 4.4 log | <10 | >4.3 log | $3.1.0 \times 10^4$ | 0.8 log |
| A Criteria | + | | + | | + | | – | |
| B Criteria | + | | + | | + | | – | |
| Veterinary Use | + | | + | | + | | + | |

TABLE 12

Preservative efficacy of octenidine dihydrochloride (0.001 mg/mL)
Octenidine Dihydrochloride - 0.001 mg/mL

|  | S. aureus | | P. aeruginosa | | C. albicans | | A. brasiliensis | |
|---|---|---|---|---|---|---|---|---|
| Inoculum | $10 \times 10^6$ | | $1.2 \times 10^6$ | | $1.9 \times 10^5$ | | $1.9 \times 10^5$ | |
| T0 | $1.6 \times 10^5$ | | $7.5 \times 10^4$ | | $1.7 \times 10^5$ | | $2.4 \times 10^5$ | |
| 6 h | $1.6 \times 10^2$ | 3.8 log | $1.0 \times 10^3$ | 3 log | – | | – | |
| 24 h | <10 | >5 log | $1.0 \times 10^4$ | 3 log | – | | – | |
| 7 d | $2 \times 10^2$ | 3.7 log | $>3.3 \times 10^6$ | 0 log | 20 | 4 log | $1.7 \times 10^5$ | 0 log |

TABLE 12-continued

Preservative efficacy of octenidine dihydrochloride (0.001 mg/mL)
Octenidine Dihydrochloride - 0.001 mg/mL

|  | S. aureus | | P. aeruginosa | | C. albicans | | A. brasiliensis | |
|---|---|---|---|---|---|---|---|---|
| 14 d | $1.4 \times 10^2$ | 3.9 log | $>3.3 \times 10^6$ | 0 log | 10 | 4.3 log | $1.4 \times 10^5$ | 0.1 log |
| 28 d | 40 | 4.4 log | $>3.3 \times 10^6$ | 0 log | <10 | >4.3 log | $1.0 \times 10^5$ | 0.3 log |
| A Criteria | – | | – | | + | | – | |
| B Criteria | + | | – | | + | | – | |
| Veterinary Use | + | | – | | + | | + | |

TABLE 13

Summary of the preservative efficacy of octenidine

| | S. aureus | | | | P. aeruginosa | | | | C. albicans | | | | A. brasiliensis | | | |
|---|---|---|---|---|---|---|---|---|---|---|---|---|---|---|---|---|
| | | | | | | | | Dose (mg/mL) | | | | | | | | |
| Criteria | A | B | C | D | A | B | C | D | A | B | C | D | A | B | C | D |
| A criteria | | + | | | + | + | | | | + | | | – | – | – | – |
| B criteria | | – | | | | | | | | | | | – | – | + | + |
| USP | | – | | | | | | | | | | | | + | | |
| Veterinary use | | – | | | | | | | | | | | | | | |

A = 0.001 mg/mL
B = 0.01 mg/mL
C = 0.1 mg/mL
D = 1 mg/mL

TABLE 14

Overview of polymer and octenidine as vaccine preservatives

| Criteria | Pol(imido-amine) | Octenidine |
|---|---|---|
| Efficacy | MIC ≤0.25 µg/ml<br>Broad spectrum<br>Non antibiotics active | MIC ≤1 µg/ml<br>Broad spectrum<br>Non antibiotics active |
| Innocuity | Cytotoxicity data and pretox IV/IP/oral on mouse/rat MTD around 10 to 25 mg/kg $IC_{50}$ hemolysis >5000 mg/ml Favorable therapeutic index | Cytotoxicity data failed to demonstrate any adverse effect to wound healing $LD_{50}$ on rat = 10 mg/kg |
| Food safety assessment | Absence of MRL<br>Oral, IP and IV toxicity data available | MRL<br>(cutaneous treatment)<br>ADI = 37.5 µg/person<br>EMA/CVMP/735219/2009 |

MTD was evaluated by IP, IV, and oral in mouse and rat; and by intramammary in cow (see US 2014/0271526 (to Merial, Inc.) and US 2014/0275469 (to Genzyme)).
Therapeutic Index (TI) was estimated as a multiple of the MIC for the Mouse (IP) MTD.

Example 3

Oil-in-Water Emulsion Preservative Study

Methodology.

For each concentration of preservative (or preservative combination), dilution neutralization and other testing was carried out as disclosed in Example 1. The "TS6" formulation is an oil-in-water emulsion, described in U.S. Pat. No. 7,371,395 B2 (to Merial, Inc.; see especially Example 1). For each formulation (see Table 15), the TS6 antigen component consisted of porcine circovirus 2 (PCV2) virus-like particles (VLPs) and inactivated *Mycoplasma hyopneumoniae* (*M. hyo*) (see U.S. Pat. No. 7,371,395 B2, Examples 3 and 5).

TABLE 15

Summary of test conditions and results

| | | | Veterinary Pharmacopeia Criteria | | | | Human Pharmacopeia | |
|---|---|---|---|---|---|---|---|---|
| ID | Formula | Preservative | S. aureus | P. aeruginosa | C. albicans | A. brasiliensis | Crit. A | Crit. B |
| A | TS6 | POL 250 µg/ml | + | + | + | + | + | + |
| B | TS6 | POL 500 µg/ml | + | + | + | + | + | + |
| C | TS6 | POL 100 µg/ml +<br>Thiomersal 25 µg/ml | + | + | + | + | + | + |
| D | TS6 | Thiomersal 25 µg/ml | + | + | + | + | –* | –* |
| E | TS6 | OCT 250 µg/ml | + | – | + | + | –* | – |
| F | TS6 | POL + OCT 100/100 µg/ml | + | + | + | + | – | + |

*for *S. aureus*

Taken together, the data presented in Examples 1 to 3 (and throughout this disclosure) indicate that both the polyamide polymer and octenidine are safe and effective vaccine preservatives. Finally, Example 3 demonstrates that the polyamide polymers and octenidine are effective preservatives in a significantly challenging vaccine environment: oil-in-water emulsion. For example, this complicated formulation system presents many opportunities for unwanted interactions with proteins and surfactants, which could have impaired the preservative efficacy of the polyamide polymers and/or the octenidine. In fact, in a previous experiment Applicants showed that 100 µg/ml of either the polyamide polymer or the octenidine alone did not exhibit satisfactory preservative efficacy in this oily vaccine environment. Accordingly, it was quite unexpected to observe the positive results summarized in Table 15. And finally, the antimicrobial polyamide polymers demonstrated unexpected superior efficacy over the octenidine and the mercurial preservative, Thiomersal, in the oily vaccine environment.

Having thus described in detail preferred embodiments of the present invention, it is to be understood that the invention defined by the above examples is not to be limited to particular details set forth in the above description as many apparent variations thereof are possible without departing from the spirit or scope of the present invention.

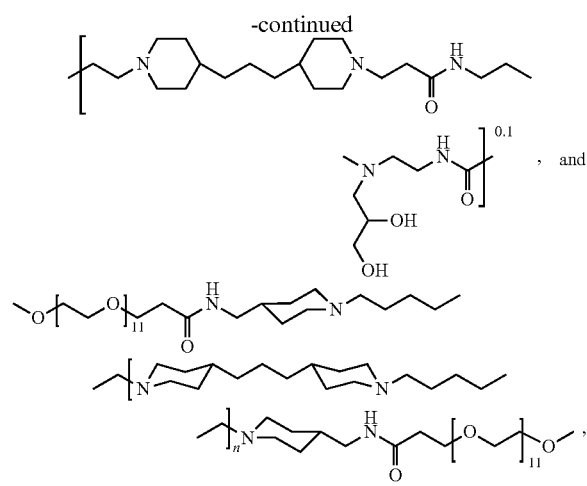

and combinations thereof, wherein n is an integer from 1 to 400; and combinations thereof; admixed in an oil-in-water emulsion wherein the API is at least one antigen wherein the formulation contains no mercurial preservative.

2. The preserved multi-dose formulation of claim 1, wherein the polyamide has the following structure:

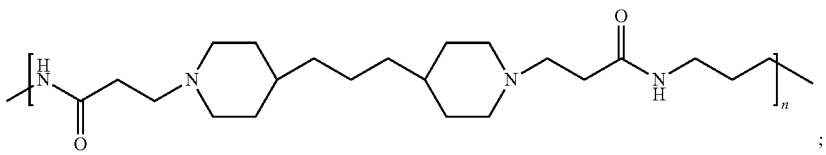

What is claimed is:

1. A preserved multi-dose formulation, wherein: the formulation comprises at least two effective doses of one or more active pharmaceutical ingredient (API) and a preservative effective amount of a non-mercurial preservative selected from the group consisting of

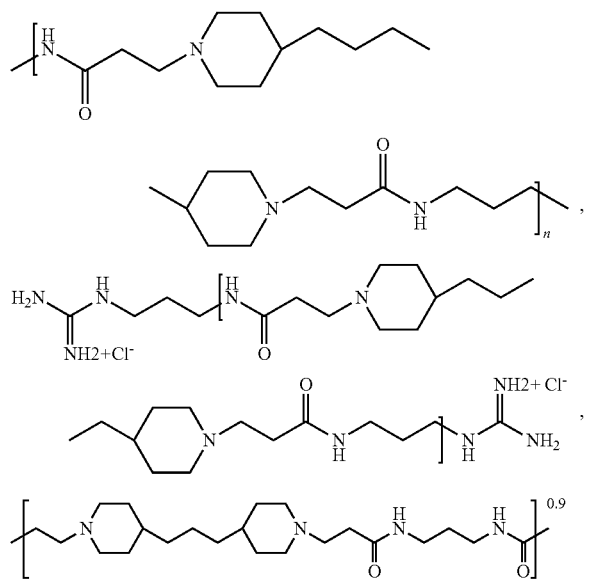

and wherein the weight average molecular weight (WAMW) is from about 1.0 kDa to about 15.0 kDa, as measured by size exclusion chromatography.

3. The preserved multi-dose formulation of claim 2, wherein the polyamide has a WAMW from about 2.0 kDa to about 10 kDa.

4. The preserved multi-dose formulation of claim 2, wherein the polyamide has a WAMW from about 2.5 kDa to about 7.76 kDa, or has a WAMW of about 7.76 kDa.

5. The preserved multi-dose formulation of claim 1, wherein the formulation comprises the antimicrobial polyamide polymer at a concentration of between about 0.1 mg/mL to about 0.25 mg/mL of formulation.

6. The preserved multi-dose formulation of claim 5, wherein the formulation comprises the antimicrobial polyamide polymer at a concentration of about 0.25 mg/mL of formulation.

7. The preserved multi-dose formulation of claim 5, wherein the formulation further comprises an adjuvant.

8. The preserved multi-dose formulation of claim 5, wherein the antigenicity of the immunogenic formulation is stable for not less than 1 year, 1.5 years, 2 years or 2.5 years; and wherein the multi-dose formulation remains stable despite at least ten usages.

9. The preserved multi-dose formulation of claim 5, wherein, following inoculation of the formulation with one or more micro-organisms, the concentration of said micro-organisms is reduced over time, wherein the formulation presents at least 1.0 log reduction from the initial microorganism count at 24 hours, at least 3.0 log reduction at 7 days from the previous value measured and not more than 0.5 log increase at 28 days from the previous value measured.

10. The preserved multi-dose formulation of claim 5, wherein, following inoculation with one or more micro-organisms, the formulation presents at least 2.0 log reduction from the initial calculated count at 6 hours after inoculation, at least 3.0 log reduction at 24 hours from the previous value measured and no recovery at 28 days.

11. The preserved multi-dose formulation of claim 5, wherein the one or more micro-organisms is selected from *P. aeruginosa, S. aureus, E. coli, B. subtilis* and combinations thereof.

12. The preserved multi-dose formulation of claim 5, wherein the formulation further comprises one or more of a buffer, a cryoprotectant, a salt, a divalent cation, a non-ionic detergent and an inhibitor of free radical oxidation.

13. The preserved multi-dose formulation of claim 5, wherein the formulation is contained within a vial.

14. A pre-filled vaccine delivery device comprising the preserved multi-dose formulation of claim 5.

15. The pre-filled vaccine delivery device of claim 14, wherein the device is a syringe and the preserved multi-dose formulation is formulated for intramuscular or subcutaneous injection.

* * * * *